United States Patent
Coleman et al.

(10) Patent No.: US 11,571,206 B2
(45) Date of Patent: Feb. 7, 2023

(54) TIBIAL PLATEAU LEVELING OSTEOTOMY SYSTEMS AND METHODS

(71) Applicants: Robert Glen Coleman, Eads, TN (US); Michael Sherman, Memphis, TN (US); Dimitri Protopsaltis, Memphis, TN (US)

(72) Inventors: Robert Glen Coleman, Eads, TN (US); Michael Sherman, Memphis, TN (US); Dimitri Protopsaltis, Memphis, TN (US)

(*) Notice: Subject to any disclaimer, the term of this patent is extended or adjusted under 35 U.S.C. 154(b) by 78 days.

(21) Appl. No.: 16/936,730

(22) Filed: Jul. 23, 2020

(65) Prior Publication Data
US 2021/0022730 A1    Jan. 28, 2021

Related U.S. Application Data

(60) Provisional application No. 62/877,458, filed on Jul. 23, 2019, provisional application No. 62/877,438, filed on Jul. 23, 2019.

(51) Int. Cl.
*A61B 17/064* (2006.01)
*A61B 17/068* (2006.01)
(Continued)

(52) U.S. Cl.
CPC ...... *A61B 17/0642* (2013.01); *A61B 17/0682* (2013.01); *A61B 17/1662* (2013.01);
(Continued)

(58) Field of Classification Search
CPC ............ A61B 17/0642; A61B 17/0643; A61B 17/0682
See application file for complete search history.

(56) References Cited

U.S. PATENT DOCUMENTS

| 4,677,973 A | * | 7/1987 | Slocum | ................ A61B 17/151 606/88 |
|---|---|---|---|---|
| 5,304,180 A | | 4/1994 | Slocum | |

(Continued)

FOREIGN PATENT DOCUMENTS

EP    2937051    10/2015

OTHER PUBLICATIONS

International Search Report and Written Opinion dated Nov. 5, 2020 for corresponding International Patent Application No. PCT/US2020/043195.

(Continued)

*Primary Examiner* — Matthew J Lawson
(74) *Attorney, Agent, or Firm* — David Meibos; Maywood IP Law

(57) ABSTRACT

Systems and methods for tibial plateau leveling osteotomy (TPLO) are disclosed. According to some embodiments, an osteotomy method may include cutting a tibia with an arcuate cut to separate a tibial plateau of the tibia from a tibial base of the tibia, rotating the tibial plateau relative to the tibial base from a first orientation to a second orientation, and, with the tibial plateau in the second orientation relative to the tibial base, securing an implant to the tibia to secure the tibial plateau to the tibial base. Securing the implant to the tibia may include embedding a first leg of the implant into the tibial base, and embedding a second leg of the implant into the tibial plateau such that the first and second legs apply compression urging the tibial plateau toward the tibial base.

20 Claims, 9 Drawing Sheets

(51) Int. Cl.
*A61B 17/16* (2006.01)
*A61B 17/17* (2006.01)
*A61D 1/00* (2006.01)
*A61B 17/68* (2006.01)

(52) U.S. Cl.
CPC ............ *A61B 17/1739* (2013.01); *A61D 1/00* (2013.01); *A61B 2017/0641* (2013.01); *A61B 2017/681* (2013.01)

(56) References Cited

U.S. PATENT DOCUMENTS

| | | | |
|---|---|---|---|
| 5,947,999 A * | 9/1999 | Groiso | A61B 17/8019 606/220 |
| 6,428,542 B1 * | 8/2002 | Michelson | A61B 17/7059 606/295 |
| 6,966,911 B2 | 11/2005 | Groiso | |
| 7,065,731 B2 | 6/2006 | Jacques et al. | |
| 7,080,339 B2 | 7/2006 | Jacques et al. | |
| 7,722,653 B2 * | 5/2010 | Young | A61B 17/8052 606/291 |
| 7,905,924 B2 | 3/2011 | White | |
| 8,021,403 B2 | 9/2011 | Wall et al. | |
| 8,454,665 B2 | 6/2013 | Sidebotham | |
| 8,518,045 B2 | 8/2013 | Szanto | |
| 8,523,921 B2 | 9/2013 | Horan et al. | |
| 8,523,949 B2 | 9/2013 | White | |
| 8,529,571 B2 | 9/2013 | Horan et al. | |
| 9,259,322 B2 | 2/2016 | Embleton et al. | |
| 9,345,469 B2 | 5/2016 | Mattchen | |
| 9,375,220 B2 | 6/2016 | Horan et al. | |
| 9,532,820 B2 | 1/2017 | Weiner et al. | |
| 9,566,103 B2 | 2/2017 | Mayer | |
| 9,585,704 B2 | 3/2017 | Alleyne | |
| 9,622,802 B2 | 4/2017 | Embleton et al. | |
| 9,622,867 B2 | 4/2017 | Embleton et al. | |
| 9,737,349 B2 | 8/2017 | Tepic et al. | |
| 9,861,408 B2 | 1/2018 | Shenoy et al. | |
| 9,955,964 B2 | 5/2018 | Mayer et al. | |
| 10,064,618 B2 | 9/2018 | Allen | |
| 10,130,481 B2 | 11/2018 | Tepic et al. | |
| 10,226,288 B2 | 3/2019 | Sidebotham et al. | |
| 10,258,396 B2 | 4/2019 | Kazanovicz et al. | |
| 10,271,839 B2 | 4/2019 | Mayer et al. | |
| 10,299,841 B2 | 5/2019 | Dunlop et al. | |
| 10,299,842 B2 | 5/2019 | Hollis et al. | |
| 10,383,625 B1 * | 8/2019 | Pirela-Cruz | A61B 17/846 |
| 11,357,553 B2 * | 6/2022 | Paton | A61B 17/8014 |
| 2002/0022844 A1 | 2/2002 | Vom Berg et al. | |
| 2006/0149275 A1 | 7/2006 | Cadmus | |
| 2006/0212035 A1 | 9/2006 | Wotton, III | |
| 2006/0229621 A1 * | 10/2006 | Cadmus | A61B 17/151 606/87 |
| 2007/0135839 A1 | 6/2007 | Cook et al. | |
| 2007/0233106 A1 | 10/2007 | Horan et al. | |
| 2008/0051791 A1 | 2/2008 | Young et al. | |
| 2009/0062800 A1 * | 3/2009 | Shano | A61B 17/0642 606/300 |
| 2009/0076513 A1 | 3/2009 | Szanto | |
| 2010/0010549 A1 | 1/2010 | Alleyne et al. | |
| 2010/0191243 A1 * | 7/2010 | Horan | A61B 17/15 606/87 |
| 2011/0208200 A1 | 8/2011 | Keffer | |
| 2011/0230919 A1 | 9/2011 | Alleyne | |
| 2011/0319994 A1 | 12/2011 | Tepic et al. | |
| 2012/0203283 A1 | 8/2012 | Wotton, III | |
| 2012/0265254 A1 | 10/2012 | Horan et al. | |
| 2012/0265256 A1 | 10/2012 | Biedermann et al. | |
| 2013/0226252 A1 | 8/2013 | Mayer | |
| 2014/0243977 A1 | 8/2014 | Tepic et al. | |
| 2015/0073475 A1 | 3/2015 | Schaller | |
| 2015/0127011 A1 * | 5/2015 | Dunlop | A61B 17/842 606/88 |
| 2017/0172637 A1 | 6/2017 | Mayer | |
| 2017/0181779 A1 | 6/2017 | Leither et al. | |
| 2017/0231193 A1 | 8/2017 | Allman | |
| 2017/0281157 A1 * | 10/2017 | Hartdegen | A61B 17/846 |
| 2018/0317984 A1 | 11/2018 | Horan et al. | |
| 2018/0325568 A1 | 11/2018 | Wotton, III | |
| 2018/0353172 A1 | 12/2018 | Hartdegen et al. | |
| 2019/0060043 A1 | 2/2019 | Tepic | |
| 2019/0117219 A1 | 4/2019 | Ritz et al. | |
| 2019/0282365 A1 | 9/2019 | Ellington et al. | |
| 2020/0000465 A1 | 1/2020 | Maclure et al. | |
| 2020/0038076 A1 | 2/2020 | Amis et al. | |
| 2020/0197005 A1 | 6/2020 | Daniel | |

OTHER PUBLICATIONS

TPLO Plate System, Surgical Technique for Tibial Plateau Leveling Osteotomy with InternalBrace Ligament Augmentation, Anthrex Vet Systems, 2019 (16 pgs).

* cited by examiner

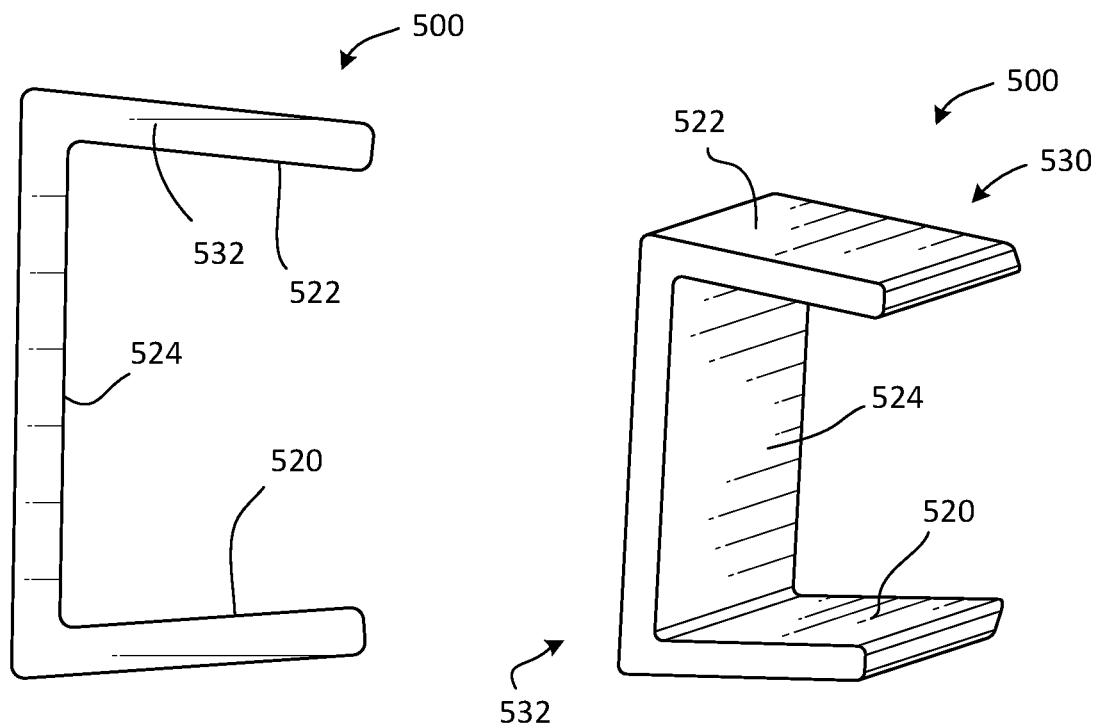
*Fig. 5A*  *Fig. 5B*
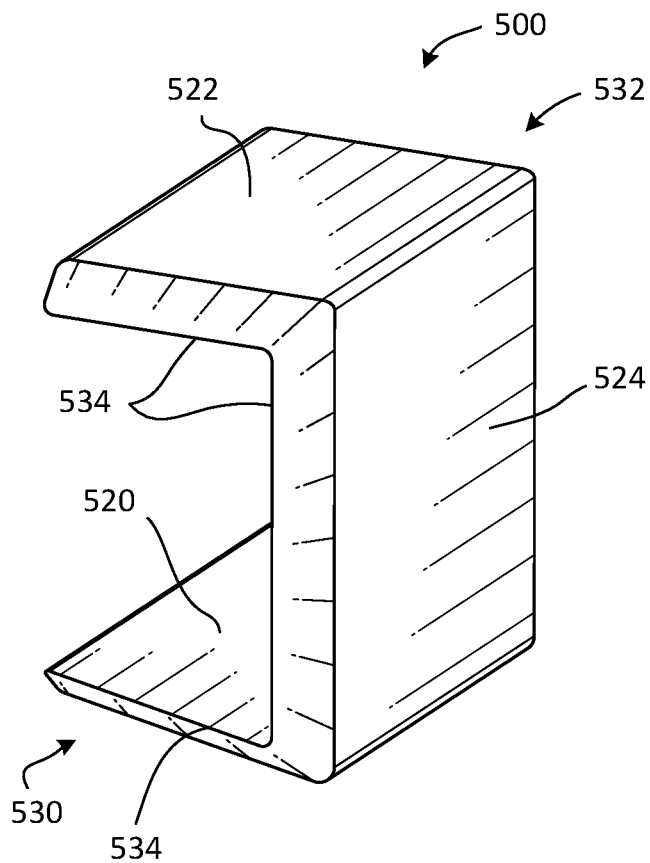
*Fig. 5C*

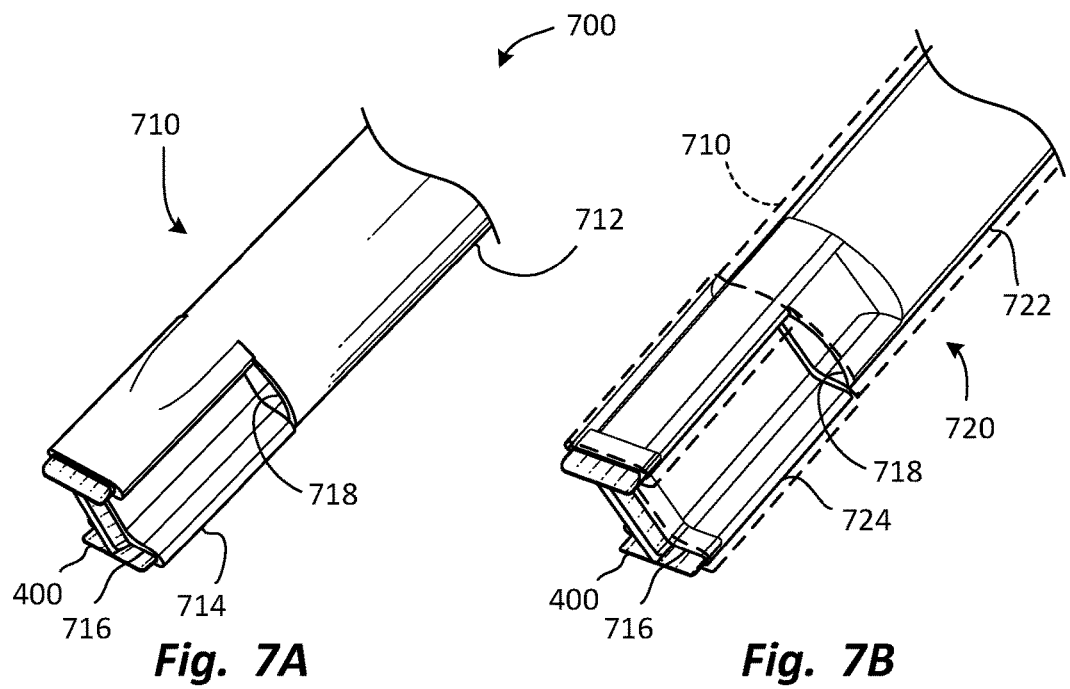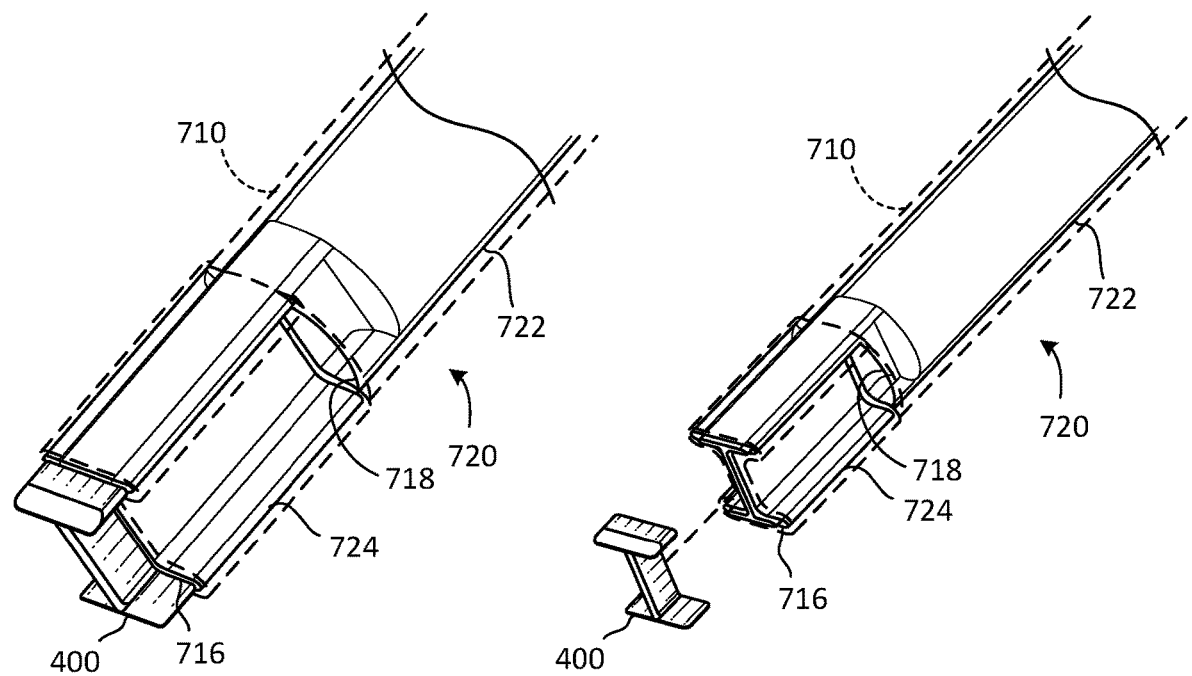

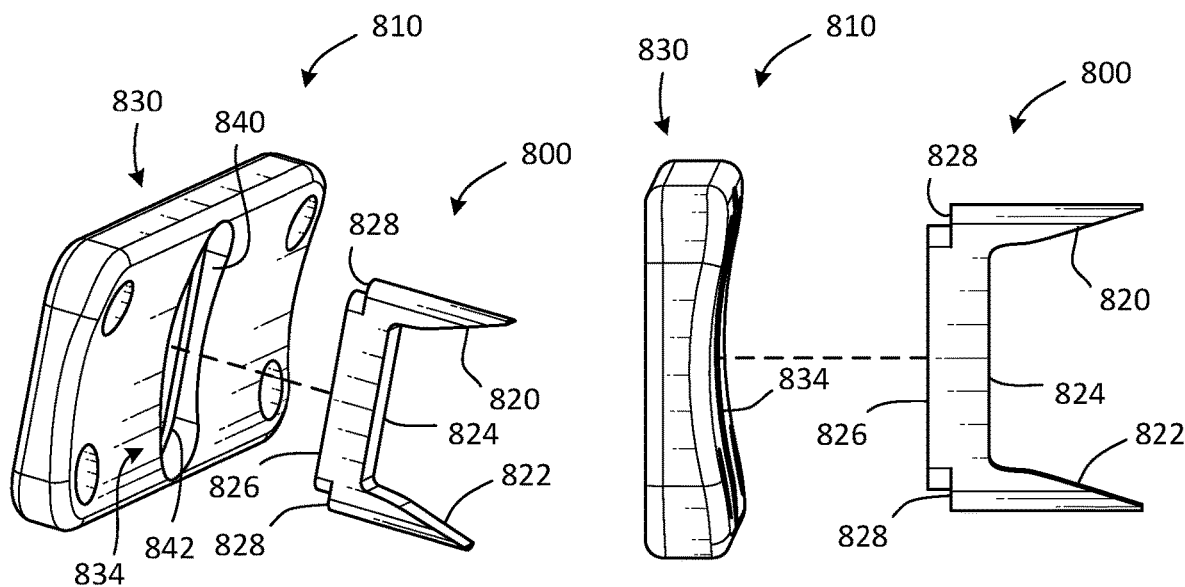
*Fig. 8A*  *Fig. 8B*
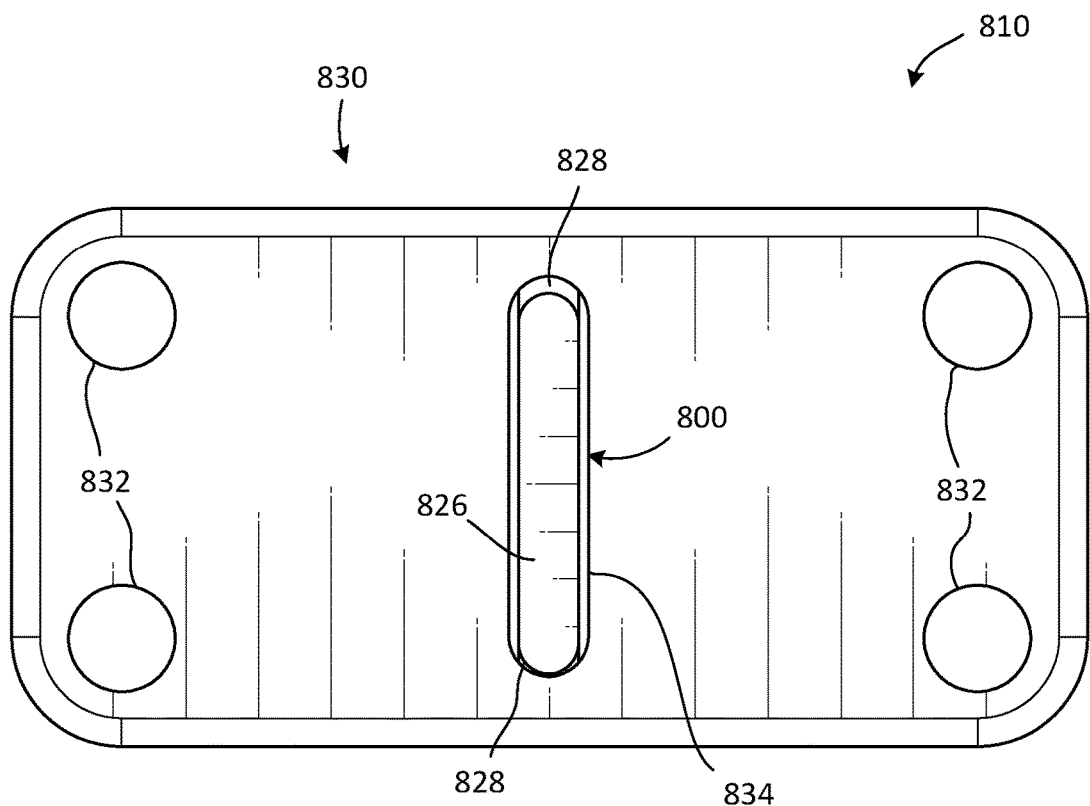
*Fig. 8C*

TIBIAL PLATEAU LEVELING OSTEOTOMY SYSTEMS AND METHODS

CROSS-REFERENCE TO RELATED APPLICATIONS

The present application claims the benefit of U.S. Provisional Patent Application Ser. No. 62/877,438, entitled DEVICE AND METHOD FOR TIBIAL PLATEAU LEVELING OSTEOTOMY, which was filed on Jul. 23, 2019, and U.S. Provisional Patent Application Ser. No. 62/877,458, entitled COMPRESSION IMPLANT AND METHOD FOR TPLO SURGERY ON THE STIFLE JOINT, which was filed on Jul. 23, 2019. The foregoing are incorporated by reference as though set forth herein in their entirety.

TECHNICAL FIELD

The present disclosure relates generally to surgical systems and methods, and more particularly, for surgical implants, instruments, and techniques for conducting tibial plateau leveling osteotomy.

BACKGROUND

Osteotomies are often performed by surgeons to realign joint mechanics in patients, both human and animal, in an attempt of avert progression of osteoarthritis and larger procedures like total joint replacement. In this disclosure, methods, implants and instruments for tibial plateau leveling osteotomy ("TPLO") are disclosed. Rotational tibial plateau leveling osteotomies are a common procedure used by orthopedic veterinarians to treat torn cranial cruciate ligaments (CCL) in canine stifle joints. This ligament corresponds to the anterior cruciate N ligament (ACL) in the human knee joint. One of the important functions for the CCL is to control the sliding of the distal femur on the proximal tibia. Unfortunately, however, for many canines the ligament partially or fully ruptures. The TPLO procedure provides a way to correct this problem. Known osteotomy procedures are described in U.S. Pat. Nos. 8,523,921, 4,677, 973, and 5,304,180.

The procedure involves (1) making a circular cut, also known as an osteotomy in the proximal tibia, separating the articulating joint surface from the rest of the tibial bone, (2) rotating the articular surface until it is more level with the ground and therefore more perpendicular to the direction of loading, and (3) fixing and stabilizing the two bone portions together in order to allow for healing (fusion) of the osteotomy. These procedures provide an alternative therapy to ligament repair procedures, and have become the standard of care for medium and large canines.

Various systems and methods have been used to secure the cut portion of the tibia to the remaining portion of the tibia. Initially, screws and wires were used for this purpose, but could be difficult to properly place and did not provide sufficient fixation.

Later, metal plates were anchored into the tibia with bone screws to span the cut in the bone. One problem with such bone plates is that they require the surgeon to manipulate the plate to conform to the tibia during the surgical procedure. This is often difficult because the plates are relatively thick and rigid, and thus are not easily bent into an acceptable shape. Furthermore, bending of the plate during the procedure can result in the screw holes becoming deformed such that they will not receive the screws needed to anchor them in place. Further, the screw holes in the plate may not be positioned for optimum fixation, and may position the screws too close to the cut in the tibia or the tibial articular surface. Further, existing TPLO plates are often long, requiring the plate to extend far distally of the osteotomy, and requiring several fixation screws.

Accordingly, many known TPLO systems and methods involve extended incisions, additional operative time, and thence, increased morbidity to the patient. There is a need for improved TPLO systems and methods that relieve these deficiencies.

SUMMARY

The various systems and methods of the present disclosure have been developed in response to the present state of the art, and in particular, in response to the problems and needs in the art that have not yet been fully solved by currently available TPLO systems. The systems and methods of the present disclosure may provide TPLO systems and methods that remedy shortcomings of prior art TPLO systems and methods.

To achieve the foregoing, and in accordance with the disclosure as embodied and broadly described herein, a method for performing a tibial plateau leveling osteotomy is disclosed. In one embodiment, the method may include carrying out an osteotomy of the tibia with an arcuate cut to separate the tibial plateau of the tibia from a tibial base of the tibia, rotating the tibial plateau relative to the tibial base from a first orientation to a second orientation, and, with the tibial plateau in the second orientation relative to the tibial base, securing an implant to the portions of tibia to secure the tibial plateau to the tibial base. The implant may be secured to the tibia by embedding a first leg of the implant into the tibial base, and embedding a second leg of the implant into the tibial plateau such that the first and second legs apply compression urging the tibial plateau toward the tibial base.

The implant may further include a bridge that connects the first leg to the second leg. Securing the implant to the tibia may include embedding only the first leg and the second leg in the tibia such that, in response to force urging rotation of the tibial plateau relative to the tibial base, away from the second orientation, the bridge is loaded in tension to resist the rotation.

The implant may further include a bridge that connects the first leg to the second leg. Securing the implant to the tibia may further include embedding the bridge in the tibial base and in the tibial plateau such that the bridge spans the arcuate cut.

The bridge may be generally perpendicular to the first leg and the second leg. Securing the implant to the tibia may include positioning the first leg and the second leg generally parallel to the arcuate cut.

Each of the first leg, the second leg, and the bridge may include a leading edge having a sharpened shape configured to penetrate the tibia.

The implant may be generally C-shaped.
The implant may be generally I-shaped.

The method may further include, prior to securing the implant to the tibia, using a cutting guide to form an aperture, shaped to receive the implant, in the tibia. The aperture may be formed by guiding motion of a cutter with a first leg portion of the cutting guide to facilitate penetration of the tibia with the first leg, guiding the cutter with a second leg portion of the cutting guide to facilitate penetration of the tibia with the second leg, and guiding the cutter with a bridge portion of the cutting guide to facilitate penetration of the tibia with the bridge.

Securing the implant to the tibia may include driving the implant into the tibia with a driver with a delivery channel that has a channel cross-sectional shape conforming to an implant cross-sectional shape of the implant.

The implant may further include a supplemental attachment feature and a bridge that connects the first leg to the second leg and to the supplemental attachment feature. Securing the implant to the tibia may further include securing the supplemental attachment feature to the tibia, displaced from the first leg and the second leg, such that the supplemental attachment feature resists rotation of the implant in response to force urging the tibial plateau to rotate, relative to the tibial base, away from the second orientation.

The supplemental attachment feature may be formed as a single piece with the first leg, the second leg, and the bridge.

The supplemental attachment feature may be separate from the first leg, the second leg, and the bridge. Securing the implant to the tibia may further include securing the supplemental attachment feature to the bridge, displaced from the first leg and the second leg.

The method may further include, after securing the implant to the tibia, securing an implant retainer to the tibia such that at least part of the implant is between the tibia and the implant retainer.

The method may further include, after securing the implant to the tibia, securing one or more additional implants to the tibia to further secure the tibial plateau to the tibial base by embedding a first additional leg of each of the one or more additional implants into the tibial base, and embedding a second additional leg of each of the one or more additional implants into the tibial plateau.

According to one embodiment, a system for performing tibial plateau leveling osteotomy may be provided. The system may include one or more implants securable to a tibia to secure the tibial base of the tibia to the tibial plateau of the tibia, wherein the tibial plateau is separated from the tibial base by an arcuate cut. Each of the one or more implants may include a first leg embeddable into the tibial base, a second leg embeddable into the tibial plateau, a supplemental attachment feature, and a bridge that connects the first leg to the second leg and to the supplemental attachment feature. The supplemental attachment feature may be displaced from the first leg and the second leg such that, with the one or more implants secured to the tibia, the supplemental attachment feature resists rotation of the implant in response to force urging the tibial plateau to rotate relative to the tibial base.

The supplemental attachment feature may be formed as a single piece with the first leg, the second leg, and the bridge.

The supplemental attachment feature may be separate from the first leg, the second leg, and the bridge. The supplemental attachment feature may further be securable to the bridge, displaced from the first leg and the second leg.

According to one embodiment, a system for performing tibial plateau leveling osteotomy may be provided. The system may include one or more implants securable to a tibia to secure the tibial base of the tibia to the tibial plateau of the tibia, wherein the tibial plateau is separated from the tibial base by an arcuate cut. Each of the one or more implants may include a first leg embeddable into the tibial base, a second leg embeddable into the tibial plateau, and a bridge that connects the first leg to the second leg. The bridge may be embeddable in the tibial base and the tibial plateau such that the bridge spans the arcuate cut. The bridge may be generally perpendicular to the first leg and the second leg. Each of the first leg, the second leg, and the bridge may include a leading edge having a sharpened shape configured to penetrate the tibia.

The system may further include a cutting guide with a first leg portion configured to guide motion of a cutter to facilitate penetration of the tibia with the first leg, a second leg portion configured to further guide motion of the cutter to facilitate penetration of the tibia with the second leg, and a bridge portion configured to further guide motion of the cutter to facilitate penetration of the tibia with the bridge.

The system may further include a driver with a delivery channel having a channel cross-sectional shape conforming to an implant cross-sectional shape of each of the one or more implants, and a pusher that can be actuated by a user to drive each of the one or more implants through the delivery channel.

These and other features and advantages of the present disclosure will become more fully apparent from the following description and appended claims or may be learned by the practice of the disclosure as set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the disclosure will be described with additional specificity and detail through use of the accompanying drawings in which:

FIGS. 5A, 5B, and 5C are rear elevation, perspective, and perspective views, respectively, of an implant according to another alternative embodiment of the present disclosure.

FIGS. 7A, 7B, 7C, and 7D are perspective views of a driver that may be used to place the implant of FIGS. 4A, 4B, 4C, and 4D, according to one embodiment.

FIGS. 8A, 8B, and 8C are perspective, perspective, and top plan views, respectively of an implant and implant retainer according to another alternative embodiment of the present disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 10F, is not intended to limit the scope of the claims, but is merely representative exemplary of exemplary embodiments of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The system and method of use in accordance with the present application may overcome one or more of the above-discussed problems commonly associated with conventional TPLO systems and methods. Specifically, TPLO systems and methods presented herein may enable TPLO surgeries to be reliably performed with smaller incisions, less intrusive implants, and shortened recovery times. These and other unique features of the system and method of use are discussed below and illustrated in the accompanying drawings.

Figures 1A, 1B:
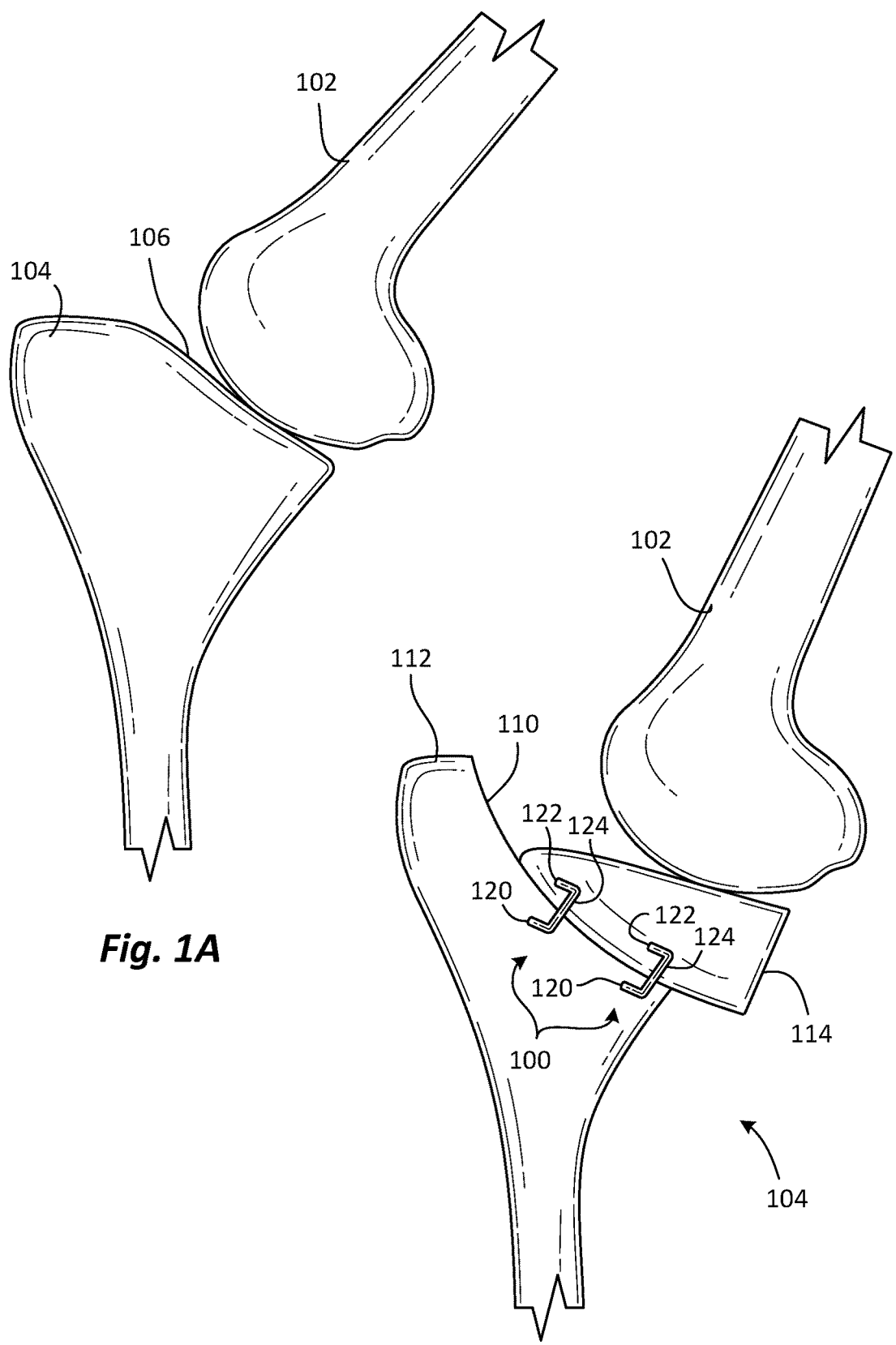
FIGS. 1A and 1B are side elevation views of a canine knee joint before and after a TPLO surgery according to one embodiment of the present disclosure.

FIGS. 1A and 1B are side elevation views of a canine knee joint before and after a TPLO surgery, respectively, according to one embodiment of the present disclosure. As shown in FIG. 1A, the joint may include a femur 102 and a tibia 104. The tibia 104 may have an articular surface 106 on which the femur 102 articulates. Ordinarily, the articular surface 106 may be angled as in FIG. 1A. This angulation may be suitable when all ligaments of the joint are functioning properly, but when the CCL is torn or otherwise damaged, the joint may be destabilized such that angulation of the articular surface 106 causes the femur 102 tends to slide off, leading to pain and poor joint function.

FIG. 1B illustrates the joint after performance of a TPLO surgery in which the tibia 104 has been cut with an arcuate cut 110, dividing the tibia 104 into a tibial base 112 and a tibial plateau 114. The arcuate cut 110 permits the tibial plateau 114 to be rotated, relative to the tibial base 112, from a first orientation (i.e., the orientation of FIG. 1A) to a second orientation in which the articular surface 106 is more horizontal. Positioning the tibial plateau 114 in the second orientation may reduce the likelihood that the damage to the ligaments of the joint will allow the femur 102 to slide off of the articular surface 106.

With the tibial plateau 114 in the second orientation relative to the tibial base 112, the tibial plateau 114 may be re-attached to the tibial base 112, and fusion may be promoted between the tibial base 112 and the tibial plateau 114. Temporary (until fusion) and/or permanent fixation may be achieved through the use of one or more implants (each of which is implant 100) secured to the tibia 104. Each implant 100 may extend across the arcuate cut 110 and may be secured to the tibial base 112 and to the tibial plateau 114 to restrict relative motion between the tibial base 112 and the tibial plateau 114.

More particularly, the implant 100 may be configured as a staple, with a first leg 120 that penetrates the tibial base 112, a second leg 122 that penetrates the tibial plateau 114, and a bridge 124 that secures the first leg 120 to the second leg 122. The implant 100 may be formed of any material(s) known to be suitable for implantation in a body, including but not limited to biocompatible metals, such as Titanium, Titanium alloys, and Nitinol, biodegradable polymers such as PLA, PGA and combinations thereof and biocompatible plastics such as polyetheretherketone ("PEEK").

In some embodiments, the implant 100 may be used to compress and/or provide rotational stability at the osteotomy site. The implant 100 may also be used for stabilization in traumatic fractures, fusions, or any situation where it is desirable to compress and/or provide rotational stability to two or more bone fragments or to two or more individual bones. For a TPLO surgery, the implant 100 may help compress the tibial plateau 114 against the tibial base 112 to promote fusion, while also helping prevent the tibial plateau 114 from rotating away from the second orientation, relative to the tibial base 112.

In some embodiments, a punch, drill, or other instrument may be used to pre-form apertures in the tibial base 112 and the tibial plateau 114 to receive the first leg 120 and the second leg 122, respectively. In the alternative, such apertures may be formed by the first leg 120 and the second leg 122 as they are pressed against the tibia 104. Optionally, the first leg 120 and/or the second leg 122 may have sharpened tips and/or edges that help penetrate the bone of the tibia 104.

The implant 100 may make use of the self-compressing nature of Nitinol, a nickel-titanium alloy that possess both super elasticity and shape memory characteristics that can be adapted to provide stabilization through compression by the implant 100. In some embodiments, the implant 100 is fabricated from superelastic Nitinol and is configured to compress the bone across the osteotomy site.

The implant 100 may be manufactured in a "closed" or compressed configuration (with the first leg 120 and the second leg 122 angled toward each other) and deformed to an "open configuration" (with the first leg 120 generally parallel to the second leg 122) prior to implantation into the tibia 104. This deformation may be accomplished by using an insertion instrument that, for example, holds the first leg 120 and second leg 122 generally parallel to each other as the implant 100 is inserted into the tibia 104. After insertion, the first leg 120 and the second leg 122 may be free to move back toward the closed configuration, compressing the tibial plateau 114 against the tibial base 112.

In some alternative embodiments, the implant 100 may be formed of one or more different materials besides Nitinol. A similar deformation may be used during implantation to provide compression to the bone.

In other alternative embodiments, the implant 100 may not be configured to provide such compression alone. Rather, the tibial base 112 and the tibial plateau 114 may be compressed together prior to implantation of the implant 100. Instruments may be used to carry out such compression; for example, one or more pins may be driven into the tibial base 112 and the tibial plateau 114, and may be drawn together (for example, with a compressor) while the implant 100 is inserted in the tibial base 112 and the tibial plateau 114. After the implant 100 has been implanted, the compression on the pins may be relieved, allowing the tibial base 112 and the tibial plateau 114 to spread apart slightly, putting the implant 100 under tension as it now serves to compress the tibial base 112 an the tibial plateau 114 together. The pins may then be removed. Alternatively, one or more lag screws, temporarily implanted, can be used to provide compression prior to placement of the implant 100.

As another alternative, the implant 100 may be formed with the first leg 120 and the second leg 122 angled toward each other, as described above. However, rather than using an instrument to draw the first leg 120 and the second leg 122 into a more parallel configuration, the first leg 120 and the second leg 122 may move into a more parallel configuration during insertion due to the placement of pre-formed apertures in the tibial base 112 and the tibial plateau 114 that are further apart than the tips of the first leg 120 and the second leg 122. The first leg 120 and the second leg 122 may be tapered such that their tips enter the holes, and further insertion spreads them toward a parallel configuration, maintaining compression on the tibial base 112 and the tibial plateau 114.

In any case, the implant 100 may exert compression on the tibial base 112 and the tibial plateau 114. This compression may help to (1) prevent relative translation or rotation between the tibial base 112 and the tibial plateau 114, and (2) promote proper healing, and potentially fusion, between the tibial base 112 and the tibial plateau 114.

In some embodiments, only one implant 100 may be used. In alternative embodiments, more than one implant 100 may be used in a single joint. Multiple implants may be placed on a single side of the joint, or distributed between opposite sides of the joint.

In some embodiments, the implant 100 may be designed and implanted such that the bridge 124 is loaded solely in tension. As mentioned previously, the tibial base 112 and the tibial plateau 114 may be compressed together during implantation, causing the bridge 124 of the implant 100 to be loaded in tension. Subsequent relative rotation of the tibial plateau 114 relative to the tibial base 112 may exert further tension on the bridge 124. This will be shown and described in connection with FIG. 2.

Figure 2:
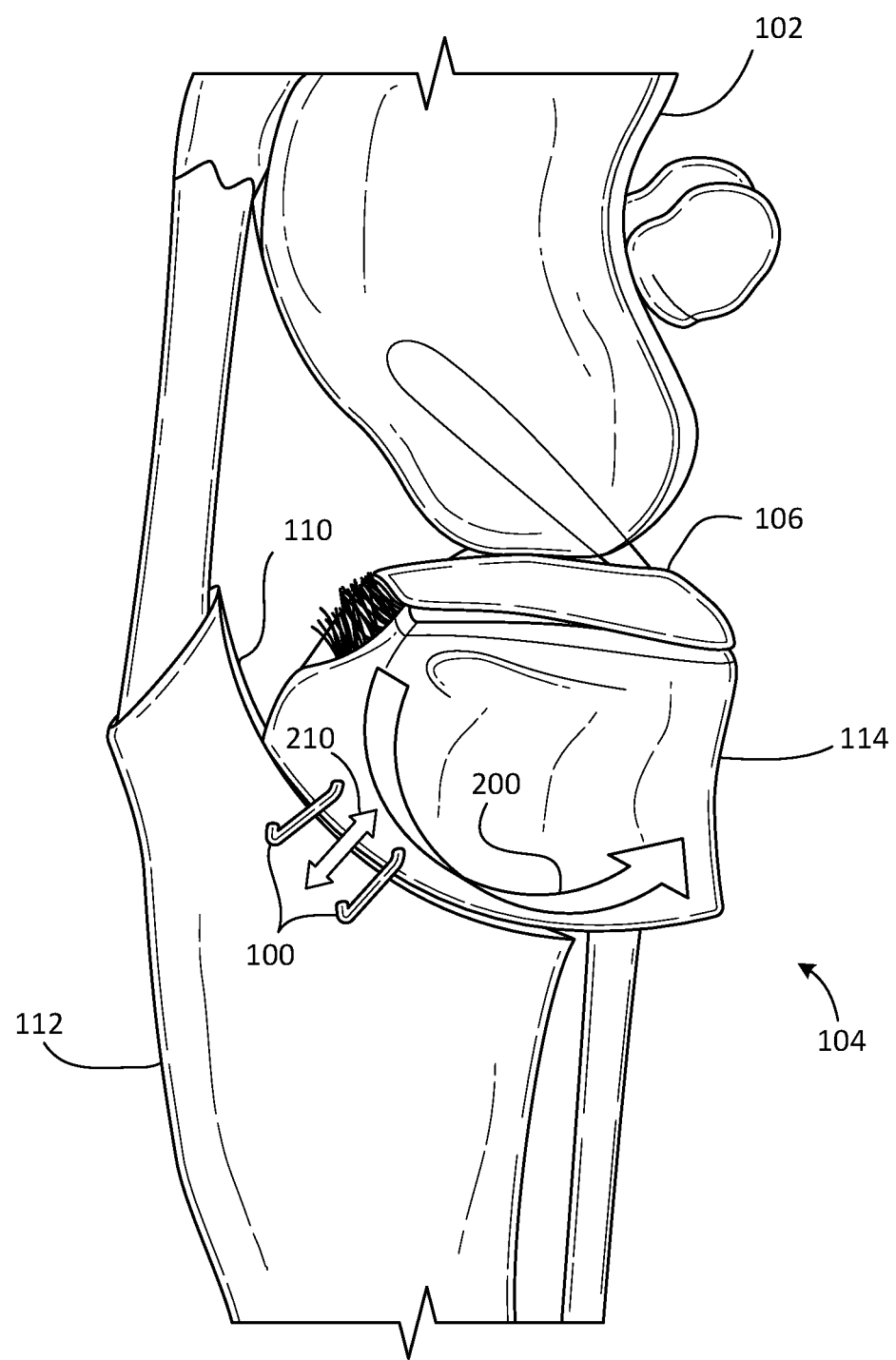
FIG. 2 is a side elevation view of the canine knee joint and implants of FIG. 1B, illustrating how the implants may resist rotation of the tibial plateau relative to the tibial base.

FIG. 2 is a side elevation view of the canine knee joint and implants of FIG. 1B, illustrating how the implant 100 may resist rotation of the tibial plateau 114 relative to the tibial base 112. As shown, downward pressure exerted by the femur 102 on the tibial plateau 114 may urge the tibial plateau 114 to rotate relative to the tibial base 112 in the direction shown by the arrow 200. Such rotation may be limited or prevented by each implant 100, which may be loaded in tension as a result, as shown by the arrow 210.

Each implant 100 may be permitted to rotate in the embodiment of FIGS. 1A-2. Such rotation may enable the bridge 124 of each implant 100 to be loaded purely in tension, rather than experiencing compressive, bending, torsional, or shear forces. Such simple loading may enable each implant 100 to be relatively compact and lightweight. For example, a pure tensile load may enable the bridge 124 to be relatively narrower than a corresponding bridge with a more complex loading pattern. In the alternative, a pure tensile load may enable the use of a material with a lower yield strength, without the need to enlarge the bridge 124 to compensate.

In some alternative embodiments, implants may be designed to avoid rotation relative to the tibia 104. Implants that are secured against rotation, relative to the tibial base 112 or the tibial plateau 114, may more effectively prevent relative motion between the tibial base 112 and the tibial plateau 114. Some examples will be shown and described in connection with FIGS. 3A, 3B, and 3C.

Figure 3A:
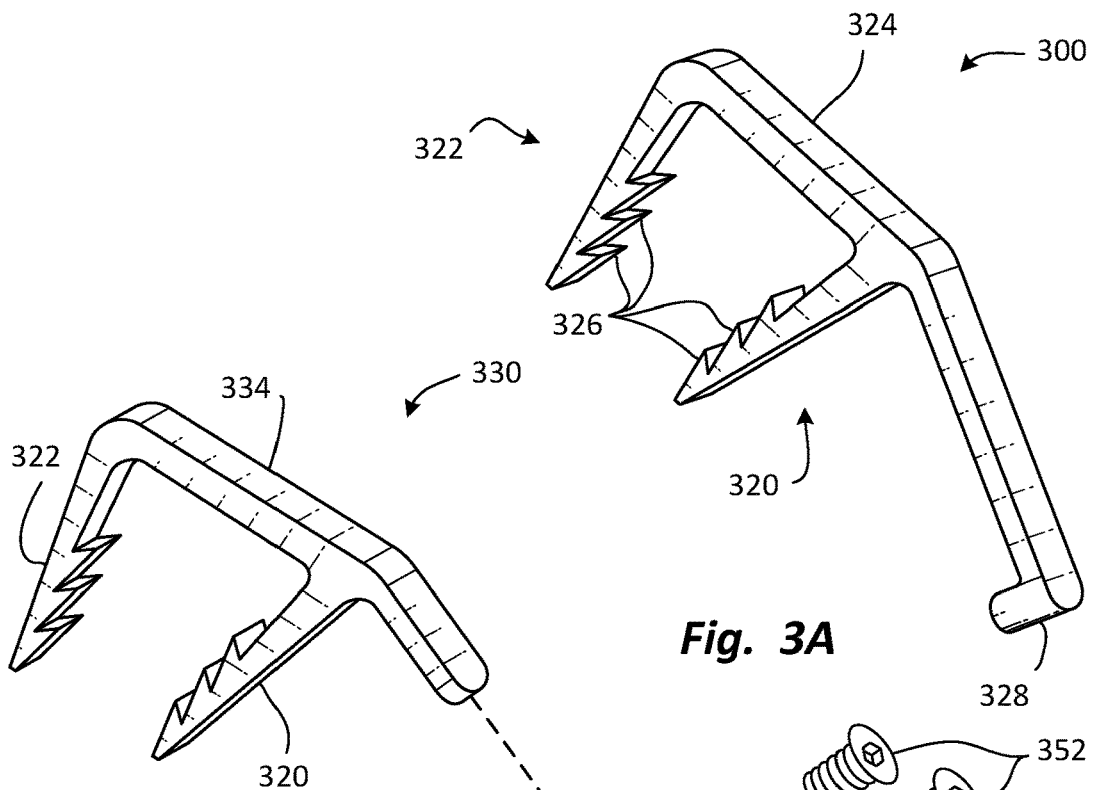
FIGS. 3A, 3B, and 3C are perspective views of implants according to alternative embodiments of the present disclosure.
Figure 3B:
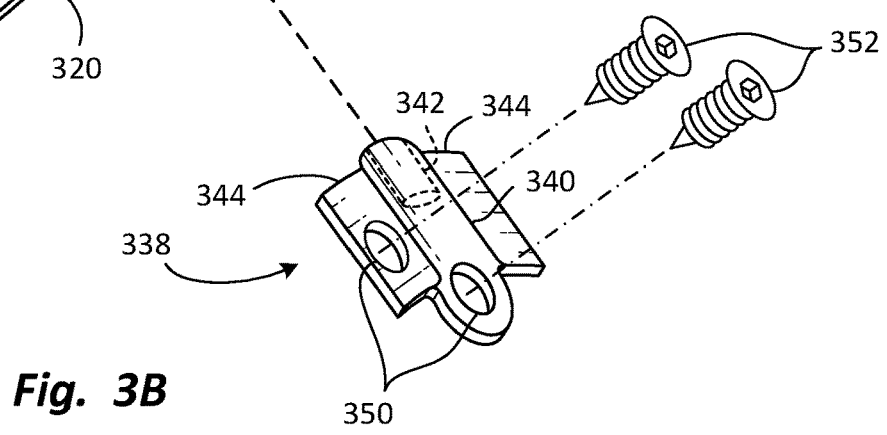
Figure 3C:
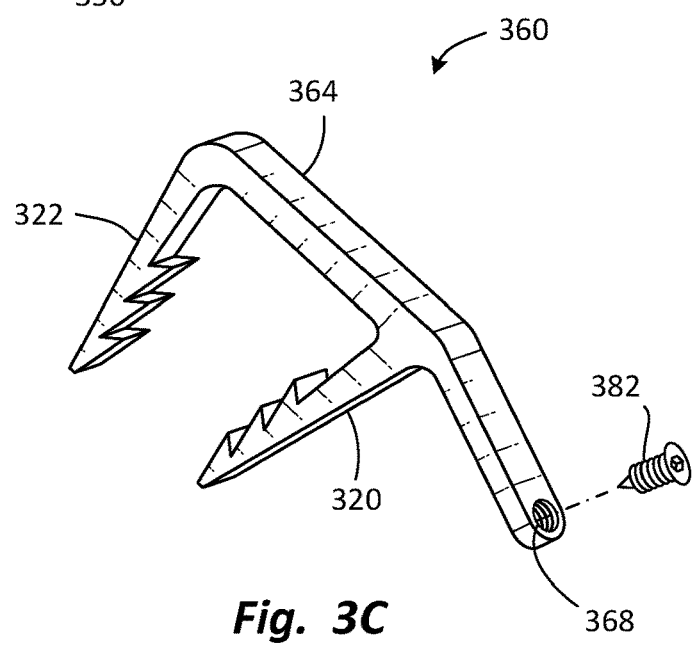
Figure 4A:
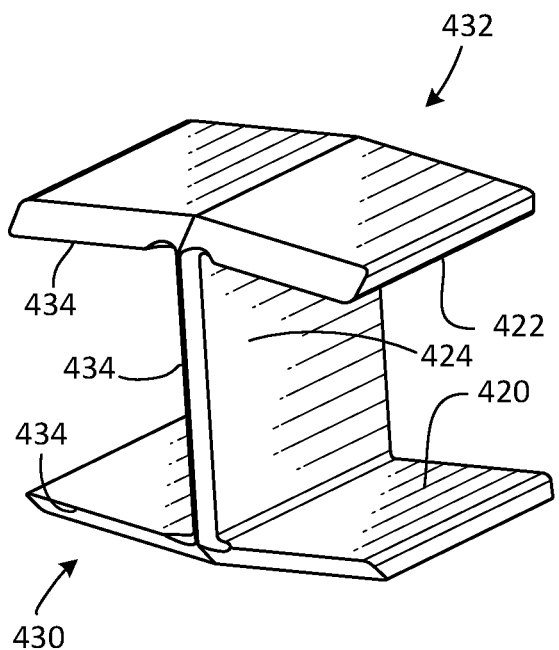
FIGS. 4A, 4B, 4C, and 4D are perspective, rear elevation, perspective, and perspective views, respectively, of an implant according to another alternative embodiment of the present disclosure.
Figure 4B:
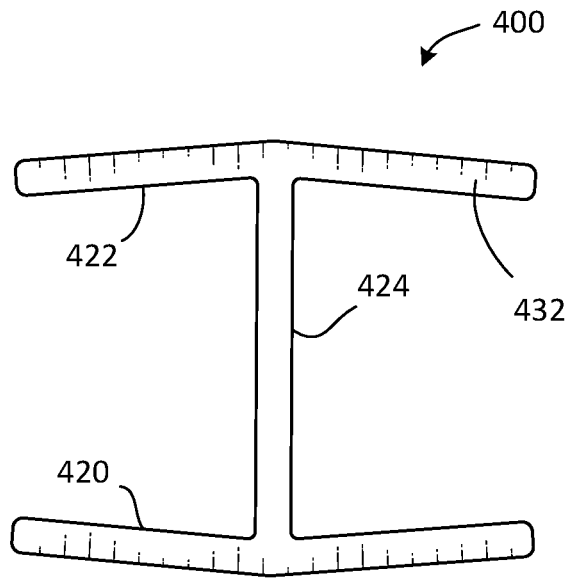
Figure 4C:
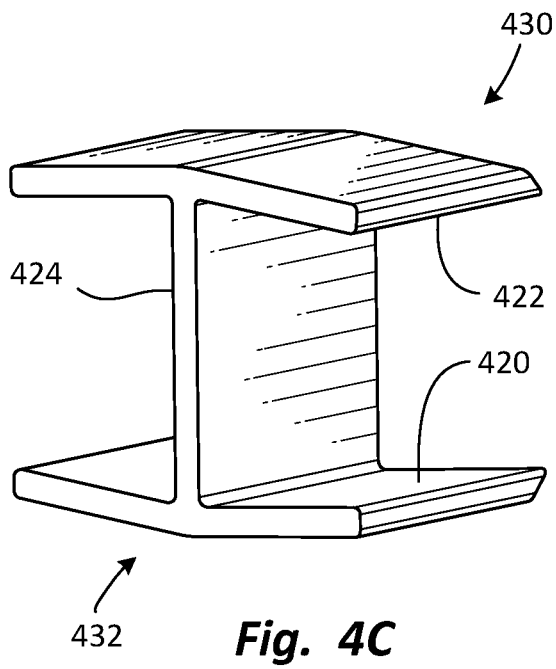
Figure 4D:
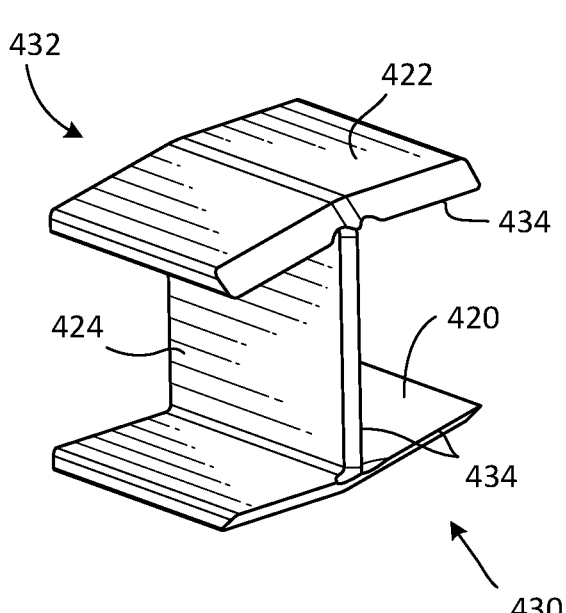
Figure 6A:
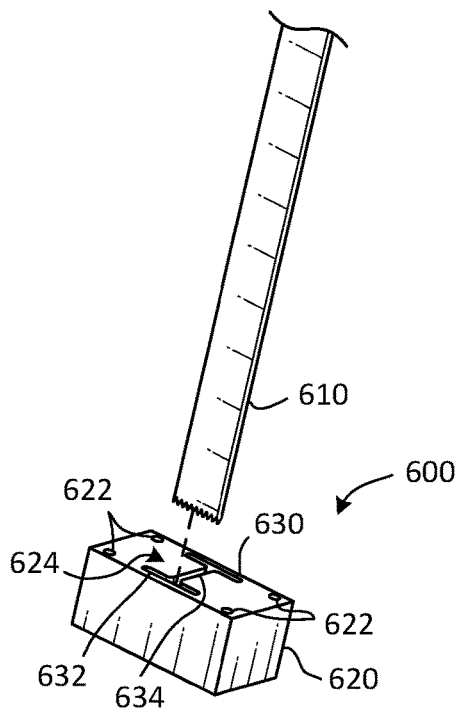
FIGS. 6A, 6B, 6C, and 6D are perspective views of a cutting guide and cutter that may be used to prepare the tibia for implantation of the implant of FIGS. 4A, 4B, 4C, and 4D, according to one embodiment of the present disclosure.
Figure 6B:
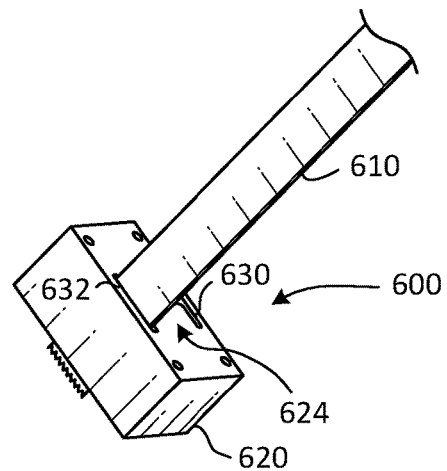
Figure 6C:
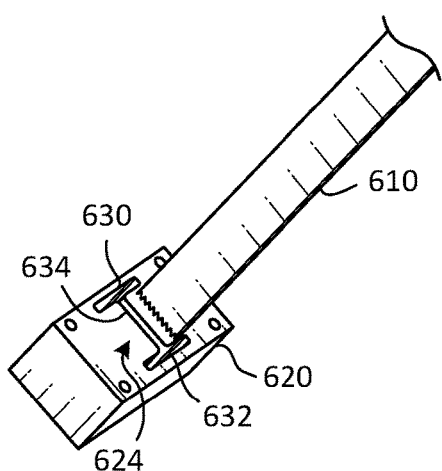
Figure 6D:
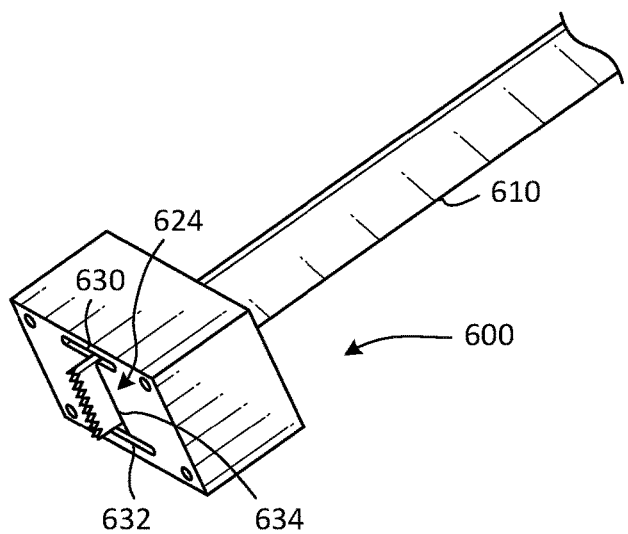

FIGS. 3A, 3B, and 3C are perspective views of an implant 300, an implant 330, and an implant 360 according to alternative embodiments of the present disclosure. The implant 300, the implant 330, and the implant 360 may each have the general shape of a staple, with a first leg 320, a second leg 322, and a bridge 324 that connects the first leg 320 to the second leg 322. However, unlike the implant 100, the implant 300, the implant 330, and the implant 360 may each include a supplemental attachment feature that helps to prevent rotation of the implant 300, the implant 330, or the implant 360 relative to the tibial base 112 and/or the tibial plateau 114.

Each of the implant 300, the implant 330, and the implant 360 may be secured to the tibial base 112 and the tibial plateau 114 to bridge the arcuate cut 110, as illustrated in FIGS. 1B and 2. The implant 300, the implant 330, and the implant 360, may each be used alone, or in groups. Implants of different types may be mixed together in a single surgery; for example, the implant 300 may be implanted alongside one or more of the implant 100 to provide additional rotational stability.

As shown, in each of implant 300, the implant 330, and the implant 360, the first leg 320 and the second leg 322 may be angled toward each other, providing the preloading described above. An inserter may spread the first leg 320 and the second leg 322 into a more parallel configuration as they are inserted into the tibial base 112 and the tibial plateau 114, respectively. In the alternative, the placement of pre-formed apertures in the tibial base 112 and the tibial plateau 114 may spread the first leg 320 and the second leg 322 apart during insertion, as described previously in connection with the implant 100. In either case, the pre-formed shape of the implant 300, the implant 330, and the implant 360 may lead to exertion of compression across the osteotomy.

As shown, the first leg 320 and the 322 may each have a plurality of teeth 326, which may be oriented generally inward. Each of the teeth 326 may have a distal ramp and a proximal ledge, lending a "harpoon shape" or "saw tooth shape" to each of the first leg 320 and the second leg 322. The teeth 326 may help the first leg 320 and the second leg 322 to lodge firmly in the bone of the tibia 104 to prevent the implant 300, the implant 330, or the implant 360 from withdrawing from the tibia 104 over time. The teeth 326 may penetrate the adjacent bone surfaces of the apertures into which the first leg 320 and the second leg 322 are inserted, causing their proximal ledges to lodge against corresponding abutments of bone.

The implant 300 may have a supplemental attachment feature 328 that is formed as a single piece with the bridge 324. The bridge 324 may thus connect the first leg 320, the second leg 322, and the supplemental attachment feature 328 together. The supplemental attachment feature 328 may be in-line with the first leg 320 and the second leg 322, as shown. In alternative embodiments, the supplemental attachment feature 328 may not be positioned in-line with the first leg 320 and the second leg 322; for example, the bridge 324 may have an angle or curve that displaces the supplemental attachment feature 328 from a line passing through the first leg 320 and the second leg 322.

The supplemental attachment feature 328 may be displaced from the first leg 320 and the second leg 322 by a distance sufficient to help resist rotation of the implant 300. The supplemental attachment feature 328 may be anchored to the tibial base 112 (for example, by securing the supplemental attachment feature 328 to the tibial base 112, distal to the first leg 320) or to the tibial plateau 114 (for example, by securing the supplemental attachment feature 328 to the tibial plateau 114, proximal to the second leg 322).

The supplemental attachment feature 328 may take the form of an integrated peg, which can be inserted into an aperture in the tibial base 112 or the tibial plateau 114. The aperture may be pre-formed through the use of a separate instrument such as drill or punch, or may be formed by pressing the integrated peg against the surface of the tibia 104 until it penetrates the bone. In some embodiments, the integrated peg may have a sharpened tip, spikes, and/or other features that facilitate penetration.

Pressure from the femur 102 may urge the tibial plateau 114 to rotate relative to the tibial base 112, as illustrated in FIG. 2. This moment may, in turn, urge the implant 300 to rotate relative to the tibial base 112 and/or the tibial plateau 114. The displacement of the supplemental attachment feature 328 from the first leg 320 and the second leg 322 may provide a longer moment arm that helps resist rotation of the implant 300, without requiring the length and bulk of a traditional bone plate. This displacement may range from 50% of the distance between the first leg 320 and the second leg 322, to 400% of the distance. More precisely, the displacement may range from 75% to 300% of the distance. Yet more precisely, the displacement may range from 100% to 200% of the distance. Still more precisely, the displacement may be about 150% of the distance, as shown in FIG. 3A.

In some embodiments, a supplemental attachment feature may include one or more parts that are not formed as a single piece with the remainder of the implant. FIGS. 3B and 3C illustrate the use of alternative supplemental attachment features that include such additional elements.

More particularly, in FIG. 3B, the implant 330 has a bridge 334 that extends to a supplemental attachment feature 338 that is separate from, and attachable to, the bridge 334. The supplemental attachment feature 338 may have a body 340 with a hole 342 that receives an extension of the bridge 334. The extension of the bridge 334 may be attachable within the hole 342 (for example, via an adhesive, set screw, or other implement, not shown), or in some embodiments, need not be fixedly secured to the body 340. The position of the body 340 along the bridge 334 may be adjustable, for example, to accommodate the shape of the bone surface to which the body 340 is to be attached, or to modify the balance between the overall length of the implant and the degree of rotational stability provided. In a longer configuration, the implant 330 may provide more rotational stability; conversely, in a shorter configuration, the implant 330 may provide less rotational stability, but may be implantable through a shorter incision.

The body 340 may have flanges 344 extending to either side to facilitate attachment to the tibial base 112 or the tibial plateau 114. Holes 350 may be formed in the body 340 and/or one or both of the flanges 344 as shown. Screws 352, which may be bone screws of any known type, may be inserted through the holes 350 to secure the body 340 to the tibial base 112 or the tibial plateau 114. In alternative embodiments, any other bone fixation system may be used, including but not limited to spikes, k-wires, cerclage cables, and/or the like.

In FIG. 3C, the implant 360 has a bridge 364 that extends to a supplemental attachment feature 368 that is attachable to the tibial base 112 or the tibial plateau 114 via a separate element, such as a screw 382. The supplemental attachment feature 368 may include a threaded or non-threaded hole that receives the screw 382.

In each of the implant 300, the implant 330, and the implant 360, the bridge 324, the bridge 334, and the bridge 364, respectively, may be bendable by the surgeon prior to implantation. Such bending may enable the supplemental attachment feature 328, the supplemental attachment feature 338, or the supplemental attachment feature 368, respectively, to be placed at a location on the tibial base 112 or the tibial plateau 114 that avoids protruding bony landmarks, aligns with high-quality bone, or the like and generally accommodates the surrounding anatomy.

In some embodiments, an implant may have a bridge that is also embedded in the bone. Such embodiments may have the advantage of additional fixation, additional rotational stability, and/or an entirely flush design whereby no part of the implant protrudes above the surface of the tibia 104. Examples will be shown and described in connection with FIGS. 4A through 5C, as follows.

FIGS. 4A, 4B, 4C, and 4D are perspective, rear elevation, perspective, and perspective views, respectively, of an implant 400 according to another alternative embodiment of the present disclosure. As shown, the implant 400 may have a first leg 420 connected to a second leg 422 via a bridge 424. The bridge 424 may be connected between the central portions of the first leg 420 and the second leg 422 such that the implant 400 has an I-shaped cross-section.

The implant 400 may have a leading end 430 and a trailing end 432. The implant 400 may be embedded into the tibia 104 by orienting the implant 400 such that the leading end 430 faces the tibia 104, and then pressing the implant 400 toward the tibia 104 such that the leading end 430 penetrates the tibia 104. The implant 400 may be further pressed into the tibia 104 until the trailing end 432 has also been embedded in the tibia 104. In the alternative, the entirety of the implant 400 need not be embedded; the trailing end 432 may protrude above the surface of the tibia 104 after implantation.

The implant 400 may be oriented and positioned such that the first leg 420 and the second leg 422 are generally parallel to the arcuate cut 110, with the first leg 420 embedded in the tibial base 112 and the second leg 422 embedded in the tibial plateau 114. The bridge 424 may cross the arcuate cut 110 to extend between the tibial base 112 and the tibial plateau 114. The bridge 424 may thus be generally perpendicular to the portion of the arcuate cut 110 that it crosses.

Advantageously, the implant 400 may also serve to resist rotation of the tibial plateau 114 relative to the tibial base 112. Force urging such rotation may load the bridge 424 of the implant 400 in shear, as the tibial plateau 114 pulls the second leg 422, relative to the first leg 420, in a direction generally parallel to the second leg 422, as shown by the arrow 200 of FIG. 2. The bridge 424 may be designed to withstand such shear loading.

The leading end 430 may be shaped to facilitate penetration of the tibia 104. More specifically, the leading end 430 may have a leading edge 434, which may have a sharpened shape designed to penetrate bone. The leading edge 434 may extend along the first leg 420, the second leg 422, and the bridge 424 at the leading end 430, as the first leg 420, the second leg 422, and the bridge 424 may all need to penetrate the bone of the tibia 104. A driver 700 may be used to facilitate this implantation, as will be shown and described subsequently in connection with FIGS. 7A, 7B, 7C, and 7D.

FIGS. 5A, 5B, and 5C are rear elevation, perspective, and perspective views, respectively, of an implant 500 according to another alternative embodiment of the present disclosure. The implant 500 may be similar in function to the implant 400 of FIGS. 4A, 4B, 4C, and 4D. As shown, the implant 500 may have a first leg 520 connected to a second leg 522 via a bridge 524. The bridge 524 may be connected between the ends of the first leg 520 and the second leg 522 such that the implant 500 has an C-shaped cross-section.

The implant 500 may be implanted in a manner similar to that of the implant 400 of FIGS. 4A, 4B, 4C, and 4D. More particularly, the implant 500 may have a leading end 530 and a trailing end 532. The implant 500 may be embedded into the tibia 104 by orienting the implant 500 such that the leading end 530 faces the tibia 104, and then pressing the implant 500 toward the tibia 104 such that the leading end 530 penetrates the tibia 104. The implant 500 may be further pressed into the tibia 104 until the trailing end 532 has also been embedded in the tibia 104, or alternatively, the trailing end 532 may protrude above the surface of the tibia 104 after implantation.

The implant 500 may be oriented and positioned such that the first leg 520 and the second leg 522 are generally parallel to the arcuate cut 110, with the first leg 520 embedded in the tibial base 112 and the second leg 522 embedded in the tibial plateau 114. The bridge 524 may cross the arcuate cut 110 to extend between the tibial base 112 and the tibial plateau 114. The bridge 524 may thus be generally perpendicular to the portion of the arcuate cut 110 that it crosses. Like the bridge 424, the bridge 524 may be loaded in shear in response to pressure urging the tibial plateau 114 to rotate relative to the tibial base 112, and may be designed to resist such loading, thereby resisting rotation of the tibial plateau 114 relative to the tibial base 112.

The leading end 530 may be shaped to facilitate penetration of the tibia 104. More specifically, the leading end 530 may have a leading edge 534, which may have a sharpened shape designed to penetrate bone. The leading edge 534 may extend along the first leg 520, the second leg 522, and the bridge 524 at the leading end 530, as the first leg 520, the second leg 522, and the bridge 524 may all need to penetrate the bone of the tibia 104.

In some embodiments, implantation of the implant 400 and/or the implant 500 may be facilitated by pre-forming an aperture in the tibia 104, with a size and shape that accommodates the implant 400 or the implant 500, as appropriate. Optionally, such a pre-formed aperture may be undersized so that the surrounding bone is necessarily compacted during insertion of the implant 400 or the implant 500. One instrument that facilitates pre-formation of an aperture for the implant 400 will be shown and described in connection with FIGS. 6A, 6B, 6C, and 6D.

FIGS. 6A, 6B, 6C, and 6D are perspective views of a cutting guide 600 and cutter 610 that may be used to prepare the tibia 104 for implantation of the implant 400 of FIGS. 4A, 4B, 4C, and 4D, according to one embodiment of the present disclosure. The cutter 610 may be of any known type, and may have a reciprocating blade designed to cut bone. The cutting guide 600 may guide motion of the cutter 610 to facilitate formation of an aperture (not shown) in the tibia 104, with a first leg portion that receives the first leg 420 of the implant 400, a second leg portion that receives the second leg 422 of the implant 400, and a bridge portion that receives the bridge 424 of the implant 400.

As shown, the cutting guide 600 may have a body 620 that can optionally be secured to the tibia 104 over the desired implantation site. The body 620 may have bone attachment features, such as attachment holes 622, that facilitate attachment of the body 620 to the tibia 104 with pins, screws, and/or other fastening devices. The body 620 may further have a guide slot 624 with an I-shaped cross section that generally matches the cross-sectional shape of the implant 400. More specifically, the guide slot 624 may have a first leg portion 630 that guides motion of the cutter 610 to form the first leg portion of the aperture, a second leg portion 632 that guides motion of the 610 to form the second leg portion of the aperture, and a bridge portion 634 that guides motion of the cutter 610 to form the bridge portion of the aperture.

The cutting guide 600 may first be placed on the tibia 104 over the desired implantation site. Then, the cutting guide 600 may be temporarily secured to the tibia 104, for example, by inserting pins into the tibia 104 through the attachment holes 622. Then, the cutter 610 may be inserted into each of the first leg portion 630, the second leg portion 632, and the bridge portion 634, in sequence, brought into contact with the tibia 104, and activated while moving the cutter 610 along the full width of each of the foregoing portions of the guide slot 624 until each portion of the aperture has been formed. The cutting guide 600 may then be removed from the tibia 104.

FIGS. 7A, 7B, 7C, and 7D are perspective views of a driver 700 that may be used to place the implant of FIGS. 4A, 4B, 4C, and 4D, according to one embodiment. The driver 700 may be used to maintain the implant 400 in the proper orientation, relative to the tibia 104, and drive it to penetrate the tibia 104.

As shown in FIG. 7A, the driver 700 may have a body 710 with a proximal end 712 and a distal end 714. The distal end 714 may have a delivery channel 716 that is shaped to receive the implant 400 and maintain the implant 400 in the desired orientation as it is advanced through the delivery channel 716, i.e., with the leading end 430 closest to the tibia 104. Thus, the delivery channel 716 may have an I-shaped cross section that corresponds to the I-shaped cross section of the implant 400. If desired, the delivery channel 716 may be slightly larger than the implant 400 so that the implant 400 can pass through the delivery channel 716 with clearance. In the alternative, the delivery channel 716 may have some slight interference with the implant 400 such that the implant 400 frictionally engages the delivery channel 716 to remain within the delivery channel 716 until it is driven distally by the surgeon. The proximal end 712 of the body 710 may have a proximal cavity 718 with a cylindrical cross-sectional shape that is larger than the delivery channel 716.

As shown in FIGS. 7B, 7C, and 7D, the driver 700 may further have a pusher 720 that can be actuated by the surgeon to drive the implant 400 distally through the delivery channel 716. The pusher 720 may have a proximal end 722 that resides generally within the proximal end 712 (i.e., the proximal cavity 718) of the body 710, and a distal end 724 that resides generally within the distal end 714 (i.e., the delivery channel 716) of the body 710. The distal end 724 may have an I-shaped cross section that matches and slides within the cross-sectional shape of the delivery channel 716, and the proximal end 722 may have a cylindrical shape that matches and slides within the cross-sectional shape of the proximal cavity 718.

In some embodiments, the proximal end 722 may protrude proximally from the proximal end 712 of the body 710 so that a surgeon can contact the proximal end 722 of the pusher 720 to drive the pusher 720 distally relative to the body 710. The proximal end 722 may have an interface (not shown) such as a handle that can be manually gripped by the surgeon, or an impact surface that can be impacted with a mallet or other tool to drive motion of the implant 400 through the delivery channel 716.

In some embodiments, the implant 400 may not be fully insertable into the delivery channel 716. A stop feature (not shown) on the implant 400 or the delivery channel 716 may be used to accomplish this by limiting motion of the implant 400 proximally into the delivery channel 716. In the alternative, a stop feature (not shown) may limit proximal motion of the pusher 720 within the body 710 so that the distal end 724 of the pusher 720 does not retreat far enough proximally within the delivery channel 716 to enable the entire depth of the implant 400 (from the leading end 430 to the trailing end 432) in the delivery channel 716. Thus, the leading end 430 of the implant 400 may protrude from the distal end 714 of the body 710 as shown. This may facilitate placement of the implant 400 prior to deployment of the driver 700, as the leading edge 434 of the implant 400 can be placed with precision at the desired implantation site before driving the implant 400 into the tibia 104 with the driver 700.

In use, the implant 400 may be inserted into the delivery channel 716 of the body 710. This step may be carried out prior to packaging and sterilization, or may be carried out by the surgeon. The implantation site may be prepared; this may optionally include formation of an aperture on the tibia 104, as described previously. The distal end 714 may be placed against the prepared bone surface, and the pusher 720 may be actuated distally to push the implant 400 through the delivery channel 716 and into the bone of the tibia 104. Once the implant 400 has been actuated out of the delivery channel 716, the driver 700 may be withdrawn, leaving the implant 400 embedded in the tibia 104. FIG. 7B shows the driver 700 with the implant 400 partially within the delivery channel 716. FIG. 7C shows the driver 700 with the implant 400 fully driven out of the delivery channel 716. FIG. 7D shows the driver 700 with the driver 700 separated from the implant 400, which may be embedded in the tibia 104.

It should be evident that cutting guide 600 and driver 700 can be easily modified from the designs presented in FIGS. 6A through 7D to accommodate implant 500, or other implants, instead of implant 400. Furthermore, implants and associated instruments are not limited to I-shaped or C-shaped cross-sections, but may have a variety of other cross-sectional shapes, including but not limited to S-shapes, V-shapes, E-shapes, L-shapes, and the like. Associated instruments may have delivery channels and/or guide slots with corresponding shapes.

According to certain embodiments, a plate or other implement may be used as an implant retainer to retain an implant properly seated across the arcuate cut 110 in the tibia 104. One exemplary embodiment will be shown and described in connection with FIGS. 8A, 8B, and 8C.

FIGS. 8A, 8B, and 8C are perspective, perspective, and top plan views, respectively of an implant 800 and implant retainer 810 according to another alternative embodiment of the present disclosure. The implant 800 may be a staple with a configuration generally similar to that of the implant 100. Alternatively, the implant 800 can include a plurality of teeth (not shown but similar to implant 300), which may be oriented generally inward. Each of the teeth may have a distal ramp and a proximal ledge, lending a "harpoon shape" or "saw tooth shape" as found on implant 300. Thus, the implant 800 may have a first leg 820, a second leg 822, and a bridge 824 that connects the first leg 820 to the second leg 822.

The implant 800 may have a generally rigid design, in which the first leg 820 and the second leg 822 do not flex significantly during insertion. As shown, the first leg 820 and the second leg 822 have generally parallel outboard surfaces, and tapered inboard surfaces by which the first leg 820 and the second leg 822 taper to points. The tapered inboard surfaces of the first leg 820 and the second leg 822 may serve to compress bone between the first leg 820 and the second leg 822 as they are inserted into the bone, thereby compressing the tibial plateau 114 against the tibial base 112 without flexure of the first leg 820 and the second leg 822.

The bridge 824 may be configured to be received and retained by the implant retainer 810. Thus, the bridge 824 may have a plateau 826 that extends proximally along part of the distance between the first leg 820 and the second leg 822. The plateau 826 may not extend to the terminal ends of the bridge 824, leaving shoulders 828 on the bridge 824, positioned on either end of the plateau 826.

The implant retainer 810 may be a bone plate that serves multiple functions, including (1) retention of the implant 800 in the bone of the tibia 104, and (2) supplemental fixation and stabilization of the tibial plateau 114 relative to the tibial base 112. Thus, the implant retainer 810 may have a body 830 with holes 832 through which fasteners, such as bone screws (not shown) can be inserted to secure the body 830 to the tibia 104. The body 830 may further have a slot 834 shaped to receive the bridge 824 of the implant 800.

Specifically, the slot 834 may have an enlarged portion 840 toward the side of the body 830 that is to face toward the tibia 104, and a lip 842 toward the opposite side of the body 830. As shown, the lip 842 may protrude inward such that, interior to the lip 842, the slot 834 may be sufficiently wide to receive the plateau 826 of the bridge 824, but not the remainder of the bridge 824. The enlarged portion 840 may be sufficiently large to receive the remainder of the bridge 824, including the shoulders 828. In an alternative embodiment, the implant retainer 810 can have multiple slots to retain multiple implants 800. The slots may be arranged in a linear arrangement in some embodiments. In alternative embodiments, they may be arranged along an arcuate pathway, for example, with a radius that matches the radius of the arcuate cut 110, so that the implants 800 can be positioned at predetermined locations, each of which enables the implant 800 to straddle the arcuate cut 110.

In use, the implant 800 may first be implanted in the tibia 104, bridging the arcuate cut 110, like the implant 100. The plateau 826 of the implant 800 may remain on top of the bone of the tibia 104. The implant retainer 810 may then be placed over and around the bridge 824, such that the plateau 826 is received within the slot 834, interior to the lip 842, as shown in FIG. 8C. Then, the implant retainer 810 may be secured to the bone, for example, by inserting bone screws into the tibia 104 through the holes 832 of the body 830. Since the implant 800 straddles the arcuate cut 110, the bone screws may be placed such that two are embedded in the tibial base 112, and the other two are embedded in the tibial plateau 114.

With the implant retainer 810 in place, the shoulders 828 may rest against the lip 842 such that the lip 842 prevents the shoulders 828, and thence the implant 800, from moving proximally with the implant retainer 810 in place. Thus, the implant retainer 810 may keep the implant 800 in place in spite of the natural tendency of the implant 800 to work its way out of the tibia 104 over time. Since the implant retainer 810 may be secured to both the tibial base 112 and the tibial plateau 114 as described above, the implant retainer 810 may further secure the tibial plateau 114 against rotation relative to the tibial base 112. The relatively small length of the implant retainer 810 may enable this to be accomplished without the drawbacks inherent in many known bone plate designs, including the need for a long incision and/or arduous efforts by the surgeon to bend the plate to match the contour of the bone.

Those of skill in the art will recognize that implant retainers of other configurations may be used in place of the implant retainer 810. Further, implant retainers may be used in connection with any of the other implant embodiments set forth in the present disclosure.

Further, any of the implants disclosed herein may have an extraction feature that facilitates removal of the implant. Tabs, threaded holes, non-threaded holes, detents, or other features may be provided to facilitate removal of the implant from the treated bone portions. Such extraction features may facilitate modification of the positioning of an implant, if it is not optimally placed in the initial insertion. Further, such extraction features may facilitate subsequent revision of the osteotomy, for example, if the tibia 104 does not heal properly and requires further treatment.

Notably, the present disclosure is not limited to implants with two legs. In some embodiments, implants may have three, four, or even more legs. Any suitable bridge structure may be used to connect the legs to each other. Such a bridge structure may include a box structure, other polygon, and/or the like.

Figure 9A:
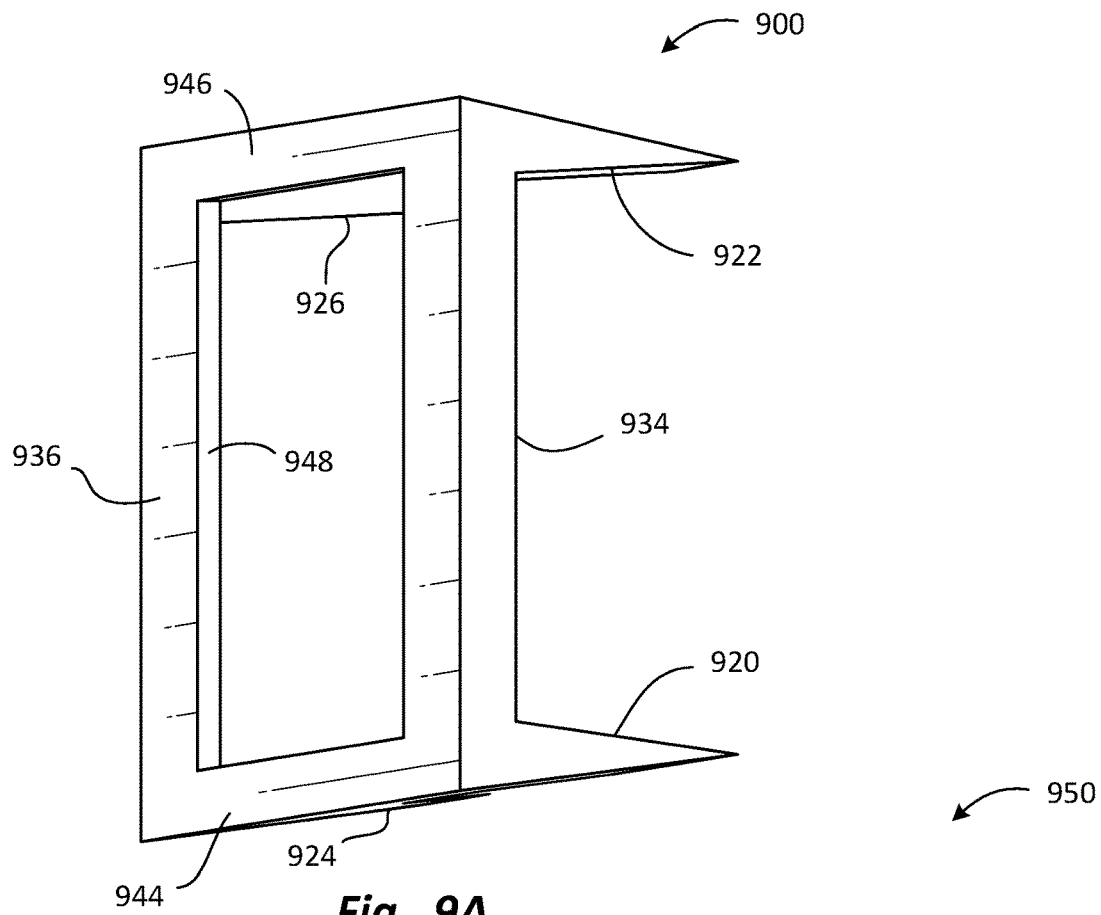
FIGS. 9A and 9B are perspective views of implants according to various further alternative embodiments of the present disclosure.
Figure 9B:
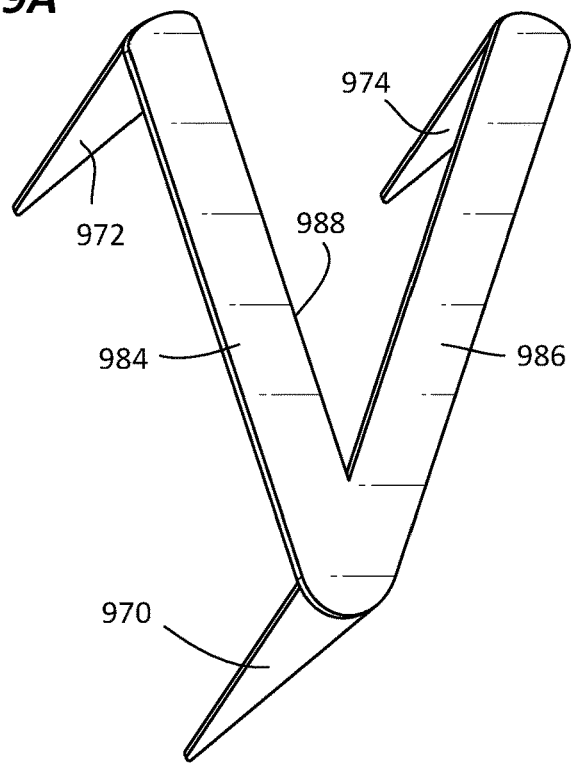

FIGS. 9A and 9B are perspective views an implant 900 and an implant 950, respectively, according to various alternative embodiments of the present disclosure. The implant 900 is an exemplary four-legged implant, and the implant 950 is an exemplary three-legged implant.

Specifically, the implant 900 of FIG. 9A may be a "box" or "table" type staple, with a first leg 920, a second leg 922, a third leg 924, and a fourth leg 926. The implant 900 may have a first bridge 934 that couples the first leg 920 to the second leg 922, and a second bridge 936, generally parallel to the first bridge 934, that couples the third leg 924 to the fourth leg 926. Further, the implant 900 may have a third bridge 944 that couples the first leg 920 to the third leg 924, and a fourth bridge 946, generally parallel to the third bridge 944, that couples the second leg 922 to the fourth leg 926.

The first bridge 934, the second bridge 936, the third bridge 944, and the fourth bridge 946 may cooperate to define an opening 948 that helps reduce the weight of the implant 900 and maintains access to the bone surface straddled by the implant 900, for example, for attachment of another implant or implant retainer (not shown) that provides supplemental fixation or helps keep the implant 900 in place.

The implant 900 may have a generally rectangular shape. Thus, the first bridge 934 and the second bridge 936 may be longer than the third bridge 944 and the fourth bridge 946. The implant 900 may be placed, according to one example, such that the first leg 920 and the third leg 924 are embedded in the tibial base 112, and the second leg 922 and the fourth leg 926 are embedded in the tibial plateau 114. Thus, the arcuate cut 110 may pass between the first leg 920 and the third leg 924, and the second leg 922 and the fourth leg 926.

The implant 950 of FIG. 9B may be a V-type staple, with a first leg 970, a second leg 972, and a third leg 974. The implant 950 may have a first bridge 984 that couples the first leg 970 to the second leg 972, and a second bridge 986, angled from the first bridge 984 in the shape of a "V," that couples the first leg 970 to the third leg 974.

The first bridge 984 and the second bridge 986 may cooperate to define an opening 988 that helps reduce the weight of the implant 950 and maintains access to the bone surface straddled by the implant 950, for example, for attachment of another implant or implant retainer (not shown) that provides supplemental fixation or helps keep the implant 950 in place.

The implant 950 may be placed, according to one example, such that the first leg 970 is embedded in the tibial base 112, and the second leg 972 and the third leg 974 are embedded in the tibial plateau 114. In the alternative, the first leg 970 may be embedded in the tibial plateau 114, and the second leg 972 and the third leg 974 may be embedded in the tibial base 112. In either case, the arcuate cut 110 may pass between the first leg 970 and, collectively, the second leg 972 and the third leg 974.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

What is claimed is:

1. A method for performing tibial plateau leveling osteotomy on a tibia comprising a tibial base and a tibial plateau, the method comprising:
   cutting the tibia with an arcuate cut to separate the tibial plateau from the tibial base;

rotating the tibial plateau relative to the tibial base from a first orientation to a second orientation; and with the tibial plateau in the second orientation relative to the tibial base, securing an implant to the tibia to secure the tibial plateau to the tibial base by:
- embedding a first leg of the implant into a region of the tibial base proximate the tibial plateau; and
- embedding a second leg of the implant into the tibial plateau such that the first and second legs apply compression urging the tibial plateau toward the tibial base,
- wherein the first leg of the implant embedded into the region of the tibial base proximate the tibial plateau comprises a most distal point of engagement of the implant with the tibial base.

2. The method of claim 1, wherein:
the implant further comprises a bridge that connects the first leg to the second leg; and
securing the implant to the tibia comprises embedding only the first leg and the second leg in the tibia such that, in response to force urging rotation of the tibial plateau relative to the tibial base, away from the second orientation, the bridge is loaded in tension to resist the rotation.

3. The method of claim 1, wherein:
the implant further comprises a bridge that connects the first leg to the second leg; and
securing the implant to the tibia further comprises embedding the bridge in the tibial base and in the tibial plateau such that the bridge spans the arcuate cut.

4. The method of claim 3, wherein the bridge is generally perpendicular to the first leg and the second leg, such that securing the implant to the tibia comprises positioning the first leg and the second leg generally parallel to the arcuate cut.

5. The method of claim 4, wherein each of the first leg, the second leg, and the bridge comprises a leading edge having a sharpened shape configured to penetrate the tibia.

6. The method of claim 4, wherein the implant is generally C-shaped.

7. The method of claim 4, wherein the implant is generally I-shaped.

8. The method of claim 4, further comprising, prior to securing the implant to the tibia, using a cutting guide to form an aperture, shaped to receive the implant, in the tibia by:
- guiding motion of a cutter with a first leg portion of the cutting guide to facilitate penetration of the tibia with the first leg;
- guiding the cutter with a second leg portion of the cutting guide to facilitate penetration of the tibia with the second leg; and
- guiding the cutter with a bridge portion of the cutting guide to facilitate penetration of the tibia with the bridge.

9. The method of claim 4, wherein securing the implant to the tibia comprises driving the implant into the tibia with a driver comprising a delivery channel with a channel cross-sectional shape conforming to an implant cross-sectional shape of the implant.

10. The method of claim 1, wherein:
the implant further comprises:
- a supplemental attachment feature; and
- a bridge that connects the first leg to the second leg and to the supplemental attachment feature; and
securing the implant to the tibia further comprises securing the supplemental attachment feature to the tibia, displaced from the first leg and the second leg, such that the supplemental attachment feature resists rotation of the implant in response to force urging the tibial plateau to rotate, relative to the tibial base, away from the second orientation.

11. The method of claim 10, wherein the supplemental attachment feature is formed as a single piece with the first leg, the second leg, and the bridge.

12. The method of claim 10, wherein:
the supplemental attachment feature is separate from the first leg, the second leg, and the bridge; and
securing the implant to the tibia further comprises securing the supplemental attachment feature to the bridge, displaced from the first leg and the second leg.

13. The method of claim 1, further comprising, after securing the implant to the tibia, securing an implant retainer to the tibia such that at least part of the implant is between the tibia and the implant retainer.

14. The method of claim 1, further comprising, after securing the implant to the tibia, securing one or more additional implants to the tibia to further secure the tibial plateau to the tibial base by:
- embedding a first additional leg of each of the one or more additional implants into the tibial base; and
- embedding a second additional leg of each of the one or more additional implants into the tibial plateau.

15. The method of claim 1, wherein:
the implant further comprises:
- a third leg;
- a first bridge that connects the first leg to the second leg; and
- a second bridge that connects the first leg to the third leg; and
the method further comprises embedding the third leg of the implant into one of the tibial base and the tibial plateau.

16. The method of claim 15, wherein:
the implant further comprises:
- a fourth leg;
- a third bridge that connects the second leg to the fourth leg; and
- a fourth bridge that connects the third leg to the fourth leg;
embedding the third leg of the implant into one of the tibial base and the tibial plateau comprises embedding the third leg in the tibial base; and
the method further comprises embedding the fourth leg in the tibial plateau.

17. A method for performing tibial plateau leveling osteotomy on a tibia comprising a tibial base and a tibial plateau, the method comprising:
cutting the tibia with an arcuate cut to separate the tibial plateau from the tibial base;
rotating the tibial plateau relative to the tibial base from a first orientation to a second orientation; and
with the tibial plateau in the second orientation relative to the tibial base, securing an implant to the tibia to secure the tibial plateau to the tibial base by:
- embedding a first leg of the implant into the tibial base; and
- embedding a second leg of the implant into the tibial plateau such that the first and second legs apply compression urging the tibial plateau toward the tibial base,
- wherein the implant further comprises a bridge having a fixed length that connects the first leg to the second leg and a supplemental attachment feature comprising an arm coupled to the bridge, wherein a length of the arm is at least 100% of a distance between the first leg and the second leg of the implant.

18. A method for performing tibial plateau leveling osteotomy on a tibia comprising a tibial base and a tibial plateau, the method comprising:
   cutting the tibia with an arcuate cut to separate the tibial plateau from the tibial base;
   rotating the tibial plateau relative to the tibial base from a first orientation to a second orientation; and
   with the tibial plateau in the second orientation relative to the tibial base, securing an implant to the tibia to secure the tibial plateau to the tibial base by:
      bending a bridge of the implant to conform a supplemental attachment feature that projects from the bridge to a surface of the tibial plateau;
      embedding a first leg of the implant into the tibial base;
      embedding a second leg of the implant into the tibial plateau such that the first and second legs apply compression urging the tibial plateau toward the tibial base; and
      securing a distal end of the supplemental attachment feature to the tibial plateau to lengthen a moment arm provided by the supplemental attachment feature that resists rotation of the tibial plateau with respect to the tibial base.

19. A method for performing tibial plateau leveling osteotomy on a tibia comprising a tibial base and a tibial plateau, the method comprising:
   cutting the tibia with an arcuate cut to separate the tibial plateau from the tibial base;
   rotating the tibial plateau relative to the tibial base from a first orientation to a second orientation; and
   with the tibial plateau in the second orientation relative to the tibial base, securing an implant to the tibia to secure the tibial plateau to the tibial base by:
      embedding a first leg of the implant into the tibial base; and
      embedding a second leg of the implant into the tibial plateau such that the first and second legs apply compression urging the tibial plateau toward the tibial base,
      wherein the implant further comprises a bridge that connects the first leg to the second leg, and
      wherein the implant has an I-shape or a C-shape when viewed along an insertion direction of the implant at an implantation site.

20. A method for performing tibial plateau leveling osteotomy on a tibia comprising a tibial base and a tibial plateau, the method comprising:
   cutting the tibia with an arcuate cut to separate the tibial plateau from the tibial base;
   rotating the tibial plateau relative to the tibial base from a first orientation to a second orientation; and
   with the tibial plateau in the second orientation relative to the tibial base, securing an implant to the tibia to secure the tibial plateau to the tibial base by:
      embedding a first leg of the implant into the tibial base;
      embedding a second leg of the implant into the tibial plateau; and
      embedding a third leg of the implant into the tibial plateau such that the first, second, and third legs apply compression urging the tibial plateau toward the tibial base,
      wherein the implant comprises a first bridge that connects the first leg to the second leg, and a second bridge that connects the first leg to the third leg, and
      wherein an entire shape of the implant is V-shaped when viewed along an insertion direction of the implant at an implantation site.

* * * * *